United States Patent
Zhang et al.

(10) Patent No.: US 10,189,769 B2
(45) Date of Patent: Jan. 29, 2019

(54) METHOD FOR PREPARATION OF PHARMACEUTICALLY ACCEPTABLE CHLOROGENIC ACID

(71) Applicant: SICHUAN JIUZHANG BIOLOGICAL SCIENCE AND TECHNOLOGY CO., LTD, Chengdu, Sichuan (CN)

(72) Inventors: Jie Zhang, Sichuan (CN); Liang Zhang, Sichuan (CN); Wang Huang, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days.

(21) Appl. No.: 15/520,356

(22) PCT Filed: Nov. 26, 2014

(86) PCT No.: PCT/CN2014/092262
§ 371 (c)(1),
(2) Date: Apr. 19, 2017

(87) PCT Pub. No.: WO2016/082122
PCT Pub. Date: Jun. 2, 2016

(65) Prior Publication Data
US 2017/0334828 A1    Nov. 23, 2017

(51) Int. Cl.
*B01D 9/00* (2006.01)
*B01D 9/04* (2006.01)
*C07C 35/14* (2006.01)
*C07C 39/10* (2006.01)
*C07C 67/48* (2006.01)
*C07C 67/52* (2006.01)
*C07C 67/56* (2006.01)
*A61K 31/216* (2006.01)
*C07C 69/732* (2006.01)

(52) U.S. Cl.
CPC ............ *C07C 67/52* (2013.01); *A61K 31/216* (2013.01); *B01D 9/0022* (2013.01); *B01D 9/04* (2013.01); *C07C 35/14* (2013.01); *C07C 39/10* (2013.01); *C07C 67/48* (2013.01); *C07C 67/56* (2013.01); *C07C 69/732* (2013.01); *B01D 2009/0086* (2013.01)

(58) Field of Classification Search
CPC ......... C07C 67/52; C07C 35/14; C07C 39/10; C07C 69/732; B01D 9/0022; B01D 9/04; B01D 2009/0086
See application file for complete search history.

(56) References Cited

FOREIGN PATENT DOCUMENTS

| CN | 1646112 A | 7/2005 |
|---|---|---|
| CN | 101805261 A | 8/2010 |
| CN | 102399146 A | 4/2012 |
| CN | 102476997 * | 5/2012 |
| CN | 103183616 B | 12/2014 |
| CN | 104496815 A | 4/2015 |

OTHER PUBLICATIONS

English translation of CN102476997, May 30, 2015, pp. 1-3 (Year: 2012).*
Wang et a., "Purification of caffeic acid, chlorogenic acid and luteolin from Caulis Lonicerae by high-speed countercurrentchromatography," Separation and Purification 63 (2008) 721-724 (Year: 2008).*
Chenxu Tian et al., "Separation and Identification of Chlorogenic Acid and Related Impurities by High Performance Liquid Chromatography-Tandem Mass Spectrometry", Chinese Journal of Chromatography, vol. 25 No. 4, Jul. 2007, pp. 496-500.

* cited by examiner

*Primary Examiner* — Pancham Bakshi
*Assistant Examiner* — Mark R Luderer
(74) *Attorney, Agent, or Firm* — Novick, Kim & Lee, PLLC; Allen Xue

(57) ABSTRACT

The present invention provides one method for the preparation of pharmaceutically acceptable chlorogenic acid, which comprises the following steps: a. Treating the sample aqueous solution; b. Freezing; c. Thawing and filtering; d. Treating the residue organic phase; e. Concentrating and crystallizing; f. Choosing the number of times to repeat steps a-e according to the variability of chlorogenic acid content in samples; g. Drying. If the chlorogenic acid extract is isolated and purified using this method, water-soluble impurities and liposoluble impurities can be well removed, that allows the impurity content of final products has fulfilled the requirements for medicine; meanwhile, the procedures of this method are simple, and organic solvents can be recycled for further use, with low cost. This method can be applied for the further isolation and purification of chlorogenic acid extract obtained by various ways, especially for the preparation of pharmaceutically acceptable chlorogenic acid.

11 Claims, No Drawings

METHOD FOR PREPARATION OF PHARMACEUTICALLY ACCEPTABLE CHLOROGENIC ACID

TECHNICAL FIELD

The present invention relates to one method for the preparation of pharmaceutically acceptable chlorogenic acid.

BACKGROUND ART

Chlorogenic acid shows a wider antibacterial action, but can be inactivated in vivo by proteins. Analogous to caffeic acid, chlorogenic acid can improve the central excitation of rats by oral administration or intraperitoneal injection. Chlorogenic acid may intensify the small bowel peristalsis for rats and mice, and the uterus tension of rats. It shows choleretic effect, and can promote the bilification of rats. Chlorogenic acid has an allergization for human, and inhalation of the plants dust containing it may cause asthma, dermatitis and so on. At present, many isolation and purification methods of chlorogenic acid have been reported, such as the application number CN201010558366 entitled "the production method for preparation of chlorogenic acid by freezing, concentrating, crystallizing". Said invention disclosed one production method of chlorogenic acid crystals, that belonged to a new method for the concentration of natural product extract solution, and during the process of isolation and purification of natural products, that can be used in the concentration of aqueous solution and in the crystal isolation of compounds. The inventors made 50% solution of chlorogenic acid in methanol crystallize at 0° C., filtered out crystals, and the crystal mother liquid was frozen at −50° C. Then, the obtained ice was taken out, and crushed into powder using ice flaker. The ice powder was subjected to centrifugal separation by a centrifugal separator, to produce the solution of chlorogenic acid in methanol at high concentration. Then, to the resulted solution, was added water, to obtain 50% solution of chlorogenic acid in methanol. This solution was placed at 0° C. to crystallize, and crystals were isolated and subjected to vacuum freeze-drying, to provide chlorogenic acid at a content of more than 98%. Application number CN201210543580 entitled "one method for the preparation of chlorogenic acid from leaves of *Lonicerahypoglauca*" disclosed one production technology of simultaneously extracting asperuloside and chlorogenic acid from leaves of *Eucommia ulmoides*. Dried *Eucommia ulmoides* leaves were used as raw materials, and purified asperuloside was produced by the following process technology: extracting with the aid of water bath heating, loading on the column, eluting, concentrating, dynamically extracting, crystallizing, recrystallizing, etc; after crystallizing, the acetone mother solution was further concentrated and combined with the thick paste from dynamic extraction, to extract chlorogenic acid. The application number CN201010135116 (entitled "one method for the preparation of purified chlorogenic acid from leaves of *Eucommia ulmoide*") related to one method for the preparation of purified chlorogenic acid from leaves of *Eucommia ulmoide* and reported the process technology: extracting by macerating in deionized water at room temperature, pressing (or centrifuging), enriching by macroporous adsorption column chromatography, extracting with ethyl acetate, recrystallizing in deionized water.

General methods for purification of chlorogenic acid also include resin column chromatography, polyamide column chromatography, gel chromatography, high performance liquid chromatography, crystallization and recrystallization, etc. Resin column chromatography can enrich and purify chlorogenic acid, but this method cannot ensure that the purity of sample and impurities conform the requirements for medicine; polyamide column chromatography has an ability of well isolating chlorogenic acid and flavones, and leading to higher purity of chlorogenic acid, but the operation is trouble, the elution time is long, the cost is high, the materials are not easily regenerated, and the investment for industrialization is larger; gel chromatography can produce high purity of chlorogenic acid, but considering the high price and the low yield of products, it is hard for gel to be used in the industrial production; high performance liquid chromatography (HPLC) can provide high purity of chlorogenic acid, but due to high technical requirements and the low yield, HPLC is still in the laboratory stage; crystallization and recrystallization are a general purification method, and this method can enrich and purify chlorogenic acid, but one solvent is usually used for the purifying process of crystallization and recrystallization, and the impurity removed by this purification is rather special, thus it is almost impossible to perform a purification from impurities with different polarity. Crystallization and recrystallization show stronger selectivity for extracts, and cannot be widely used for all extracts prepared by different process. Some references have reported the purifying method of crystallization and recrystallization using combined solvents, and impurities with different polarity can be removed by adjusting the types and the ratios of combined solvents, realizing the object of purification. This method can get rid of impurities with different polarity in the extract, but because there are great difficulties in recovering solvent combinations, this method also has some limitations. Meanwhile, the combined solvents remain in products, that may bring a potential safety hazard.

CONTENTS OF THE INVENTION

The technical solution of the present invention provides one method for the preparation of chlorogenic acid, which includes the following steps:

a. Preparing sample aqueous solution: the sample is dissolved in purified water to prepare the solution of chlorogenic acid at a concentration ranging from 20 mg/ml to 2000 mg/ml, and filtered; in which the sample is extracted from leaves of *Eucommia ulmoides* and then isolated to have a chlorogenic acid concentration of no less than 60%; the preparation temperature is lower than 60° C.;

b. Freezing: the filtrate is frozen at a temperature of below 0° C. until it fully becomes ice;

c. Thawing and filtering: the ice obtained by freezing is thawed under the conditions of 5-60° C. temperature, and the temperature of thawing solution is up to 5° C., then the solution is filtered;

d. Treating the residue organic phase: the residue obtained by filtration is dissolved in organic solvent, then filtered; in which the organic solvent is selected from any one of methyl acetate, ethyl acetate, propyl acetate, and butyl acetate; the solution temperature is up to 60° C.;

e. Concentrating and crystallizing: the organic solution is concentrated under the conditions of low temperature and negative pressure, until small amount of precipitation forms, then the solution is allowed to stand for crystallizing; the concentration temperature is up to 60° C., and the vacuum degree is 0.04 Mp or above;

f. Choosing the number of times to repeat steps a-e according to the variability of chlorogenic acid content in samples; when the content in the extract is 60-80%, steps a-e are repeated twice; when the content in the extract is 80-90%, steps a-e are repeated once; when the content in the extract is more than 90%, it is not necessary to repeat steps a-e;

g. Drying: after the crystals are filtered out, they are dried at low temperature; the dry temperature is up to 60° C., and drying is performed under normal or negative pressure. Further preferably, the method includes the following steps:

a. Preparing sample aqueous solution: the sample is dissolved in purified water to prepare the solution of chlorogenic acid at a concentration of 500 mg/ml, and filtered; in which the sample is extracted from leaves of *Eucommia ulmoides* and then isolated to have a chlorogenic acid content of 90%; the preparation temperature is 40° C.;

b. Freezing: the filtrate is frozen at a temperature of below 0° C. until it fully becomes ice;

c. Thawing and filtering: the ice obtained by freezing is thawed at the temperature of 25° C., and the temperature of thawing solution is up to 5° C., then the solution is filtered;

d. Treating the residue organic phase: the residue obtained by filtration is fully dissolved in organic solvent, then filtered; in which the organic solvent is ethyl acetate; the solution temperature is 60° C.;

e. Concentrating and crystallizing: the organic solution is concentrated under the conditions of low temperature and negative pressure, until a small quantity of precipitation forms, then the solution is allowed to stand for crystallizing; the concentration temperature is 60° C., and the vacuum degree is 0.08 Mp;

f. Drying: after the crystals are filtered out, they are dried at low temperature; the dry temperature is 60° C., and drying is performed under normal pressure.

The present invention further provides the chlorogenic acid prepared by the method mentioned above.

In which, the content of chlorogenic acid is more than 98%, and it contains 1-6 related substances, including 5-caffeoylquinic acid, 4-vinylcatechol, caffeic acid, 4-caffeoylquinic acid, 3-coumaroylquinic acid, and methylated compound of chlorogenic acid, with a content of less than 0.5%.

The present invention used the method of combining water and organic solvents, and utilized the dissolubility difference between chlorogenic acid and water-soluble impurities when they are dissolved in water at different temperatures. The water-soluble impurities are removed by the way of freezing the water phase and then thawing; after that, the dissolubility difference in organic solvents between chlorogenic acid and liposoluble impurities is used for removing liposoluble impurities by the way of concentrating organic solution and then crystallizing. The chlorogenic acid extract is isolated and purified using two solvents with different polarity, that can well get rid of water-soluble and liposoluble impurities in the extract, to ensure that the content of impurities in final products conforms the medicinal requirements; at the same time, the procedures of this method are simple, and organic solvents can be recovered for further use, with an advantage of low cost. This method is suitable for further isolation and purification of all chlorogenic acid extracts obtained by various ways, especially for the preparation of pharmaceutically acceptable chlorogenic acid.

EXAMPLES

Example 1 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 500 mg/ml, and filtered; in which the sample is extracted from leaves of *Eucommia ulmoides* and then isolated to have a chlorogenic acid content of 90%; the preparation temperature is 40° C.;

2. Freezing: the filtrate is frozen at a temperature of below 0° C. until it fully becomes ice;

3. Thawing and filtering: the ice obtained by freezing is thawed at the temperature of 25° C., and the temperature of thawing solution is up to 5° C., then the solution is filtered;

4. Treating the residue organic phase: the residue obtained by filtration is fully dissolved in organic solvent, then filtered; in which the organic solvent is ethyl acetate; the solution temperature is 60° C.;

5. Concentrating and crystallizing: the organic solution is concentrated under the conditions of low temperature and negative pressure, until a small quantity of precipitation forms, then the solution is allowed to stand for crystallizing; the concentration temperature is 60° C., and the vacuum degree is 0.08 Mp.

6. Drying: after the crystals are filtered out, they are dried at low temperature; the dry temperature is 60° C., and drying is performed under normal pressure.

Example 2 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 800 mg/ml, and filtered; in which the sample is extracted from leaves of *Eucommia ulmoides* and then isolated to have a chlorogenic acid content of 60%; the preparation temperature is 50° C.;

2. Freezing: the filtrate is frozen at a temperature of below 0° C. until it fully becomes ice;

3. Thawing and filtering: the ice obtained by freezing is thawed at the temperature of 10° C., and the temperature of thawing solution is up to 5° C., then the solution is filtered;

4. Treating the residue organic phase: the residue obtained by filtration is fully dissolved in organic solvent, then filtered; in which the organic solvent is propyl acetate; the solution temperature is 60° C.;

5. Concentrating and crystallizing: the organic solution is concentrated under the conditions of low temperature and negative pressure, until a small quantity of precipitation forms, then the solution is allowed to stand for crystallizing; the concentration temperature is 60° C., and the vacuum degree is 0.07 Mp.

6. The procedures of steps a-e are repeated twice;

7. Drying: after the crystals are filtered out, they are dried at low temperature; the dry temperature is 60° C., and drying is performed under normal pressure.

Example 3 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 20 mg/ml, and filtered; in which the sample is extracted from leaves of *Eucommia ulmoides* and then isolated to have a chlorogenic acid content of 85%; the preparation temperature is 20° C.;

2. Freezing: the filtrate is frozen at a temperature of below 0° C. until it fully becomes ice;

3. Thawing and filtering: the ice obtained by freezing is thawed at the temperature of 5° C., and the temperature of thawing solution is up to 5° C., then the solution is filtered;

4. Treating the residue organic phase: the residue obtained by filtration is fully dissolved in organic solvent, then filtered; in which the organic solvent is methyl acetate; the solution temperature is 20° C.;

5. Concentrating and crystallizing: the organic solution is concentrated under the conditions of low temperature and negative pressure, until a small quantity of precipitation forms, then the solution is allowed to stand for crystallizing; the concentration temperature is 40° C., and the vacuum degree is 0.04 Mp.

6. The procedures of steps a-e are repeated once;

7. Drying: after the crystals are filtered out, they are dried at low temperature; the dry temperature is 40° C., and drying is performed under normal pressure.

Example 4 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 100 mg/ml, and filtered; in which the sample is extracted from leaves of *Eucommia ulmoides* and then isolated to have a chlorogenic acid content of 72%; the preparation temperature is 30° C.;

2. Freezing: the filtrate is frozen at a temperature of below 0° C. until it fully becomes ice;

3. Thawing and filtering: the ice obtained by freezing is thawed at the temperature of 60° C., and the temperature of thawing solution is up to 5° C., then the solution is filtered;

4. Treating the residue organic phase: the residue obtained by filtration is fully dissolved in organic solvent, then filtered; in which the organic solvent is butyl acetate; the solution temperature is 60° C.;

5. Concentrating and crystallizing: the organic solution is concentrated under the conditions of low temperature and negative pressure, until a small quantity of precipitation forms, then the solution is allowed to stand for crystallizing; the concentration temperature is 60° C., and the vacuum degree is 0.09 Mp.

6. The procedures of steps a-e are repeated twice;

7. Drying: after the crystals are filtered out, they are dried at low temperature; the dry temperature is 60° C., and drying is performed under negative pressure.

Example 5 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 2000 mg/ml, and filtered; in which the sample is extracted from leaves of *Eucommia ulmoides* and then isolated to have a chlorogenic acid content of 68%; the preparation temperature is 60° C.;

2. Freezing: the filtrate is frozen at a temperature of below 0° C. until it fully becomes ice;

3. Thawing and filtering: the ice obtained by freezing is thawed at the temperature of 60° C., and the temperature of thawing solution is up to 5° C., then the solution is filtered;

4. Treating the residue organic phase: the residue obtained by filtration is fully dissolved in organic solvent, then filtered; in which the organic solvent is ethyl acetate; the solution temperature is 50° C.;

5. Concentrating and crystallizing: the organic solution is concentrated under the conditions of low temperature and negative pressure, until a small quantity of precipitation forms, then the solution is allowed to stand for crystallizing; the concentration temperature is 50° C., and the vacuum degree is 0.05 Mp.

6. The procedures of steps a-e are repeated twice;

7. Drying: after the crystals are filtered out, they are dried at low temperature; the dry temperature is 40° C., and drying is performed under negative pressure.

Example 6 The Method for the Preparation of Pharmaceutically Acceptable Chlorogenic Acid According to the Present Invention 1. Preparing sample aqueous solution: the sample is dissolved in purified water to prepare the solution of chlorogenic acid at a concentration of 1500 mg/ml, and filtered; in which the sample is extracted from leaves of *Eucommia ulmoides* and then isolated to have a chlorogenic acid content of 95%; the preparation temperature is 60° C.;

2. Freezing: the filtrate is frozen at a temperature of below 0° C. until it fully becomes ice;

3. Thawing and filtering: the ice obtained by freezing is thawed at the temperature of 60° C., and the temperature of thawing solution is up to 5° C., then the solution is filtered;

4. Treating the residue organic phase: the residue obtained by filtration is fully dissolved in organic solvent, then filtered; in which the organic solvent is propyl acetate; the solution temperature is 60° C.;

5. Concentrating and crystallizing: the organic solution is concentrated under the conditions of low temperature and negative pressure, until a small quantity of precipitation forms, then the solution is allowed to stand for crystallizing; the concentration temperature is 60° C., and the vacuum degree is 0.08 Mp.

6. Drying: after the crystals are filtered out, they are dried at low temperature; the dry temperature is 60° C., and drying is performed under negative pressure.

Example 7 The Quality of Pharmaceutically Acceptable Chlorogenic Acid of Examples 1-6 According to the Present Invention The Content Test Method:
Experiment on Chromatographic Conditions and System Suitability Using octadecyl-bonded silica gel as fillers; 0.1% formic acid solution-acetonitrile (92:8) as mobile phase; detection wavelength 215 nm; theoretical plates 3000, calculated as the chlorogenic acid peak; the resolution of chlorogenic acid peak and adjacent impurity peaks conforming the requirements;

Assay

Suitable amount of sample was taken out and accurately weighed, then dissolved in the mobile phase to prepare 10 µg/ml solution, that was used as the test solution. 20 µl of test solution was accurately measured and injected into liquid chromatograph, and its chromatogram was recorded; in addition, suitable amount of reference substance of chlorogenic acid was taken out and accurately weighed, then dissolved in the mobile phase to prepare 10 µg/ml solution, that was determined as the test solution; using the external standard method, the content can be calculated according to the peak areas;

The Test Method of Impurities:

Suitable amount of sample was taken out and accurately weighed, then dissolved in the mobile phase to prepare 0.5 mg/ml solution, that was used as test solution; 1 ml of test solution was transferred to 100 ml volumetric flask using a pipette, and diluted to the scale by addition of mobile phase, that was used as the control solution; suitable amount of reference substance of caffeic acid was taken out and accurately weighed, then dissolved in the mobile phase to prepare 2 µg/ml solution, that was used as the reference solution; using the same chromatographic conditions as the content test, 20 µl of the control solution was injected to the liquid chromatograph, and adjusting the detectability allowed the peak height of main constituent to be 20% of measuring range, then 20 µl of the test solution, the control solution, and the solution of reference substance were accurately measured, respectively, and injected into the liquid chromatograph, followed by recording the chromatogram till the retention time is 3 times that of main constituent; if there was caffeic acid peak in the chromatogram of test solution, it was calculated using the external standard method; if there were other impurities, they were calculated using self-control method.

TABLE 1

The quality of pharmaceutically acceptable chlorogenic acid of examples 1-6

| | Related substances (%) | | | | | | |
|---|---|---|---|---|---|---|---|
| Example | 5-caffeoyl-quinic acid | 4-vinyl-catechol | caffeic acid | 4-caffeoyl-quinic acid | 3-coumaroyl-quinic acid | methylated chlorogenic acid | Content (%) |
| Example 1 | — | — | — | — | 0.016 | — | 99.91 |
| Example 2 | 0.032 | 0.081 | 0.064 | 0.056 | 0.223 | 0.115 | 99.25 |
| Example 3 | — | 0.063 | — | — | 0.152 | — | 99.64 |
| Example 4 | 0.042 | 0.098 | 0.025 | — | 0.133 | — | 99.49 |
| Example 5 | — | 0.192 | 0.123 | — | 0.257 | — | 99.14 |
| Example 6 | — | 0.246 | 0.081 | — | 0.163 | — | 99.34 |

The invention claimed is:

1. A method for the preparation of pharmaceutically acceptable chlorogenic acid, comprising:
   a. extracting an extract containing chlorogenic acid from leaves of *Eucommia ulmoides*; treating the extract to obtain a sample having a concentration of chlorogenic acid of no less than 60% by weight;
   b. dissolving the sample in purified water to obtain a first solution having a concentration of chlorogenic acid ranging from 20 mg/ml to 2000 mg/ml; and filtering the solution to obtain a filtrate and a filtride;
   c. freezing the filtrate;
   d. thawing the frozen filtrate and keeping the thawed filtrate at a temperature of above freezing to up to 5° C.;
   e. dissolving a filtride in an organic solvent to obtain a second solution; filtering the second solution to obtain an organic solution, wherein the organic solvent is selected from the group consisting of methyl acetate, ethyl acetate, propyl acetate, and butyl acetate;
   f. condensing the organic solution at an elevated temperature and under vacuum until forming a precipitant; resting the organic solution to form crystals in the organic solution; and
   g. filtering crystals from the organic solution; drying the crystals under vacuum or standard pressure.

2. The method according to claim 1, wherein, in step (a), the chlorogenic acid concentration in the sample is 90% by weight and the chlorogenic acid concentration in the first solution is 500 mg/ml.

3. The method according to claim 1, wherein the chlorogenic acid crystals comprise more than 98% by weight of chlorogenic acid and one or more impurities selected from the group consisting of 5-caffeoylquinic acid, 4-vinylcatechol, caffeic acid, 4-caffeoylquinic acid, 3-coumaroylquinic acid, and a methylated compound of chlorogenic acid.

4. The method according to claim 3, wherein each of the one or more impurities is of less than 0.5% by weight.

5. The method according to claim 3, wherein the chlorogenic acid crystals comprise more than 99% by weight of chlorogenic acid.

6. The method according to claim 1, wherein, in step (d), the thawing temperature is 5-60° C.

7. The method according to claim 1, wherein, in step (e), the organic solvent is ethyl acetate.

8. The method according to claim 1, wherein, in step (e), the dissolving is carried out at a temperature of 20-60° C.

9. The method according to claim 1, wherein, in step (f), the condensing is carried out at a temperature of 40-60° C. and under a vacuum of 0.04-0.09 Mp.

10. The method according to claim 1, wherein, in step (g), the drying is carried out at 40-60° C.

11. The method according to claim 1, wherein, when the sample contains 60%-80% by weight of chlorogenic acid, steps (b) to (e) are carried out twice.

* * * * *